United States Patent [19]

Smargiassi

[11] 4,141,356
[45] Feb. 27, 1979

[54] RESPIRATOR SYSTEM AND METHOD

[75] Inventor: Paul R. Smargiassi, Riverside, Calif.

[73] Assignee: Bourns, Inc., Riverside, Calif.

[21] Appl. No.: 852,760

[22] Filed: Nov. 18, 1977

Related U.S. Application Data

[63] Continuation of Ser. No. 696,677, Jun. 16, 1976, abandoned.

[51] Int. Cl.² .......................................... A61M 16/00
[52] U.S. Cl. ...................... 128/145.8; 128/DIG. 17; 128/210
[58] Field of Search ............... 128/145.8, 145.6, 145.5, 128/142.2, 188, DIG. 17, DIG. 29, 2.08

[56] References Cited

U.S. PATENT DOCUMENTS

| | | | |
|---|---|---|---|
| 2,418,034 | 3/1947 | Kizaur | 128/142.2 |
| 3,736,949 | 6/1973 | Wolter et al. | 128/145.8 |
| 3,741,208 | 6/1973 | Jonsson et al. | 128/145.6 |
| 3,802,417 | 4/1974 | Lang | 124/2.08 |
| 3,903,881 | 9/1975 | Weigl | 128/145.8 |
| 3,916,889 | 11/1975 | Russell | 128/145.8 |
| 3,976,064 | 8/1976 | Wood et al. | 128/145.8 |
| 3,976,065 | 8/1976 | Durkan | 128/145.8 |
| 4,003,377 | 1/1977 | Dahl | 128/145.8 |

Primary Examiner—Henry J. Recla
Attorney, Agent, or Firm—Paul H. Ware; William G. Becker

[57] ABSTRACT

A respirator system with both assisted and spontaneous breathing modes. A control circuit responds to the patient's breathing pattern to alternate the system between the two modes in accordance with a predetermined alternation pattern. The control circuit is adjustable, enabling the frequency of assisted breaths to be gradually reduced so that the patient can be weaned away from the respirator and safely resume normal breathing under his own power. The invention also includes the operating method contemplated for such a system.

27 Claims, 2 Drawing Figures

RESPIRATOR SYSTEM AND METHOD

This application is a continuation of application Ser. No. 696,677 filed June 16, 1976, now abandoned.

BACKGROUND OF THE INVENTION

1. Field of the Invention

This invention relates to medical respirators, and more particularly to a respirator system and method having an interruptable breath assist mode in which delivery of breathing gas to a patient is initiated by the patient attempting to inhale.

2. Description of the Prior Art

Many respirators employ an "assist" mode to promote healthy patient breathing in which the patient's breath activity is monitored and a volume of air forced into his lungs when a breath attempt is detected. The assisted breaths are generally provided at steady rate until the patient is able to breathe on his own and it is safe to disconnect the respirator. These systems are capable of providing the patient with a sufficient amount of air to maintain a safe oxygen supply for as long as he is unable to breathe under his own power.

A problem may arise, however, in disconnecting the respirator. If the patient is left on his own too soon, he will be unable to breathe adequately and must be reconnected to the respirator without delay. On the other hand, the respirator may be left in place longer than is really necessary. In this case, in addition to any discomfort to the patient or unavailability of the apparatus for other patients that may be occasioned, the patient's return to unassisted breathing, which is generally a gradual process in which the patient builds up capacity breath by breath, may actually be retarded.

An alternation between spontaneous (i.e., a patient initiated and maintained positive pressure breath in which the patient controls all the parameters such as tidal volume, pulmonary pressure, flow rate, etc., except the blending of the breathing gases, i.e., the fractional inspriatory oxygen concentration ($FIO_2$), whereas on the other hand, an assisted, sometimes referred to as simply as assist breath, is one delivered to a patient in response to an effort to breath put forth by a patient when he is too weak to maintain the effort so as to obtain a full volume of air unassisted. Thus, the ventilator in an assist mode controls all the breathing parameters except the time of delivery of the breath. A controlled, sometimes simply control, breath, in contrast to both spontaneous and assist breaths, is one in which all breathing parameters are controlled by the ventilator including the time of delivery of the breath.) and assisted breathing has been achieved in an existing system by providing a constant air stream from which the patient can draw breaths upon demand, and superimposing thereon an involuntary breath assist mechanism which forces a predetermined amount of air into the patient's lungs at regular intervals independent of the patient's spontaneous breathing. Such a system may be adapted to wean a patient away from an assisted breathing mode by gradually increasing the interval between forced breaths. However, it is unresponsive to the patient's minute-by-minute spontaneous breathing pattern, since an assisted breath is produced at the preset time regardless of the spontaneous breathing rate. In addition, there is a possibility of excess pressure being produced when an assisted breath is produced on top of a spontaneous breath, at which time the patient's lungs already contain an appreciable amount of air.

Other systems have been used to interrupt a regular pattern of assisted breaths, although not necessarily for the purpose of weaning a patient from the respirator. For example, a binary counter has been used to initiate a sigh (larger than normal air volume) breath after a series of 32, 64, or 128 assisted breaths of normal volume. While it has been found desirable to provide a "sigh" control in the respirator system to periodically break the constant breathing rate, such a mechanism does not contribute towards reducing the patient's dependency on the respirator.

In another prior art device alternate spontaneous and assisted breathing air conduits are provided. This respirator is normally operated in the assist mode, but the spontaneous breath conduit opens to override the assist mechanism if the patient begins to breathe on his own before the time for the next assisted breath. The device is most useful in the transition period when the patient first begins spontaneous breathing, but is of more limited help in the later stages of weaning a patient away from a respirator, since breath assistance is provided only if the patient fails to breathe spontaneously within a set time period.

SUMMARY OF THE INVENTION

In light of the above stated problems encountered in the prior art, the general object of the present invention is to provide a novel and improved respirator system and method for maintaining a safe and regular supply of breathing air to a patient, while at the same time being capable of gradually weaning the patient away from the respirator until he has resumed full spontaneous breathing.

Another object of the invention is the provision of a novel and improved respirator system and method for weaning a patient away from the system in a manner responsive to the patient's individual spontaneous breathing pattern, and yet provide adequate breathing assistance for as long as required.

A further object of the invention is the provision of a novel and improved respirator system having alternate spontaneous and assisted breathing modes, in which the ratio of spontaneous to assisted breathing can be adjusted to facilitate weaning of a patient away from the system.

In the accomplishment of these and other objects, the present invention provides a respirator system with both positive breath assist means and means for providing breathing gas to a patient at a pressure suitable for spontaneous breathing. A control circuit actuates the breath assist means in a predetermined intermittent manner in response to the breathing pattern obtained by a breath attempt sensing means. The spontaneous breath supply means is operably responsive to the combined presence of a sensed breath attempt and nonactuation of the breath assist means, whereby spontaneous breaths are supplied when the patient attempts to breathe and an assisted breath has not already been provided.

According to one feature of the invention, the control circuit includes resetable means to count the number of patient breath attempts and actuate the breath assist means each time the breath attempt count reaches a predetermined number. In this manner only designated ones of the patient's breath attempts can trigger the breath assist means, the remainder of the breaths being spontaneous. Means are also included to adjust the breath attempt count at which the breath assist means is actuated, thereby enabling a patient to be gradually weaned away from the respirator system by progressively increasing the interval between assisted breaths until normal breathing is achieved.

According to another feature of the invention, a first pressure sensing means senses the pressure in the breathing gas conduit system and causes a control signal to be delivered to the control circuit when the pressure falls below a first threshold level, indicative of a patient attempt to breathe. The breath assist means is actuated by the control circuit in response to the pattern of received control signals. A demand regulator which includes a valve means and a second pressure sensing means adapted to sense the pressure in the conduit system controls the flow of spontaneous breathing air, the demand regulator being adapted to open the valve means and supply spontaneous breathing air to the patient when the pressure sensed by the second sensing means falls below a second threshold level which is less than the first threshold level mentioned above. In a preferred embodiment, the first and second pressure sensing means each compare the gas pressure in the conduit system with a single reference pressure provided by a positively maintained pressure plenum which is connected to the conduit system by a bleeder means. Gas is conducted from the plenum to the conduit system at a flow rate sufficient to compensate for normally encountered gas leaks therefrom.

The invention also comprehends a novel and improved method of operating a respirator system comprising the steps of sensing patient attempts to breathe, selecting periodic nonconsecutive ones of the sensed breath attempts, actuating a breath assist means in response to each of the selected breath attempts, and actuating a spontaneous breath supply means in response to the remainder of the breath attempts. In a preferred embodiment of the method, the sensed breath attempts are counted until a predetermined number is reached, at which time the breath assist means is actuated and the count is reset to an initial amount. A repetitive pattern of alternation between assisted breaths and spontaneous breaths is thereby produced, and by progressively increasing the interval between assisted breaths the patient can be gradually and safely weaned away from the respirator system.

BRIEF DESCRIPTION OF THE DRAWINGS

Further advantages and features of the invention will be apparent to those skilled in the art from the ensuing detailed description thereof, taken together with the accompanying drawings, in which.

DETAILED DESCRIPTION OF A PARTICULAR EMBODIMENT

Figure 1:
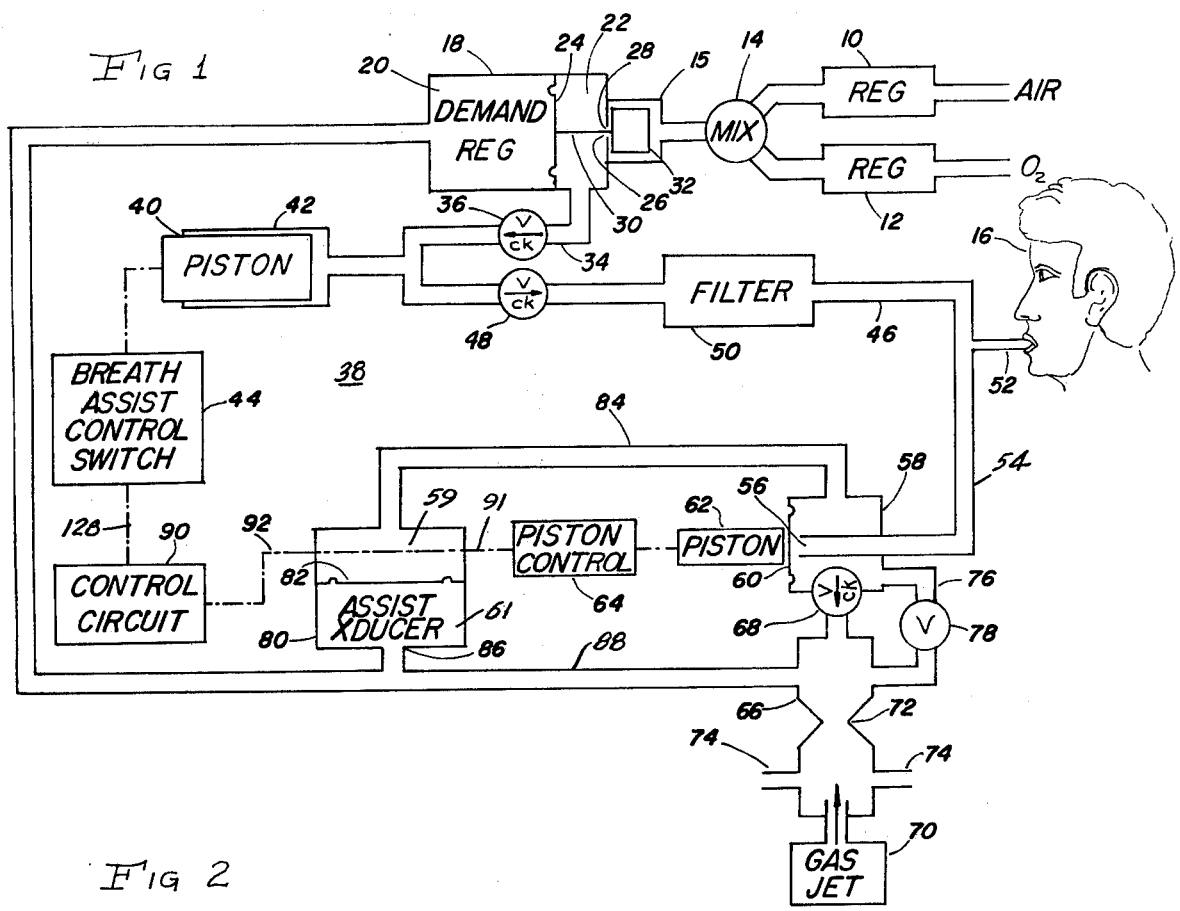
FIG. 1 is a schematic diagram of a respirator system constructed in accordance with the invention.

Referring to FIG. 1, an embodiment of the invention is shown in which air and oxygen are respectively fed through a pair of regulators 10 and 12 and delivered to a mixing valve 14 where the gases are mixed to a proportion suitable for breathing by a patient 16. The air-oxygen mixture is fed from the mixing valve 14 to the inlet chamber 15 of a demand regulator 18 which is further divided into a reference chamber 20 and a sensing chamber 22, the last two chambers being separated by a flexible, resilient diaphragm 24. Inlet chamber 15 and sensing chamber 22 are separated by a wall 26 having a central opening 28 through which a rod 30 extends from the diaphragm 24 to the interior of chamber 15. A stopper 32, affixed to the end of rod 30 within chamber 15, normally abuts the dividing wall 26 to cover opening 28, thereby preventing any flow of air between chambers 15 and 22. This flow restriction is removed when the gas pressure in chamber 22 is reduced by a predetermined amount while the gas pressure in chamber 20 remains at a constant level. In this event diaphragm 24 flexes into the area formerly occupied by chamber 22 (to the right in FIG. 1), moving stopper 32 out of contact with the dividing wall 26 and allowing gas to flow from air and oxygen supplies through regulators 10 and 12, into and through mixing valve 14 and through chamber 15 into chamber 22. The demand regulator 18 thus functions much as a scuba tank regulator; a pressure drop is produced when the user attempts to inhale, opening up a line from an air supply.

Sensing chamber 22 is connected via a conduit 34 and check valve 36 to a breath assist mechanism denoted generally by the numeral 38. The breath assist mechanism includes a piston 40 slidably lodged within a cylinder 42. A control switch 44 governs the operation of the breath assist mechanism. A negative pressure is created in sensing chamber 22 when piston 40 is drawn backward (to the left in FIG. 1), thus flexing the diaphragm 24 and thereby uncovering opening 28 to enable an air flow from air and oxygen supplies through regulators 10 and 12 into and through mixing valve 14, through chamber 22, conduit 34, and check valve 36 into cylinder 42 as long as piston 40 continues to move backward. Breath assist control switch 44 actuates the breath assist mechanism when commanded by signaling piston 40 to drive forward, thus charging the air mixture in cylinder 42 into the patient supply conduits 46 by way of check valve 49 and filter 50. The volume of gas delivered to the patient may be either a preset amount, or determined dynamically by providing well known apparatus to measure the patient's lung pressure and terminate forward movement of piston 40 when the lung pressure reaches a desired level.

A plastic tubing network 46 provides a gas conduit between the breath assist apparatus 38 and the patient 16. The conduit system includes a check valve 48 which prevents a back flow of gas from the patient to the breathing air sources, and a filter or humidyfying device 50 to treat the breathing air before delivery to the patient. An endotracheal tube 52 is fitted to the conduit system in a T connection to conduct air to and from the patient 16.

The conduit system further includes an outlet or expiratory branch 54 having an outlet port 56 enclosed within a variable pressure chamber 58, one wall of which forms a diaphragm 60 in registry with outlet port 56. A piston 62 is located to alternately flex the diaphragm 60 to a position blocking the outlet port 56 when the piston is in a forward position, and to release the diaphragm 60 and allow gas to flow out of the conduit system 54 through outlet port 56 when the piston 62 is in a retracted position. A piston control device 64 such as a solenoid under the control of an assist transducer 80 control circuit 90 causes the piston 62 to block the outlet port 56 during inspiration and uncover the port during expiration.

While the patient's breathing behavior may be sensed in a number of ways, such as by measuring the pressure within the conduit system 46 and actuating the breath assist mechanism 38 whenever the pressure falls below a particular level, in a preferred embodiment the structure shown in FIG. 1 is employed. The chamber 58 communicates with a second chamber 66 through a check valve 68 that permits a gas flow only from chamber 58 to chamber 66. The pressure within chamber 66 is positively maintained at a constant level by means of a gas jet source 70 that delivers a steady jet stream through a venturi 72 and into the chamber 66. A number of outlet orifices 74 are located between gas jet source 70 and venturi 72 to allow gas exhaled by the patient to exit from the respirator system. Gas jet source 70 is adjustable within a range that permits the pressure inside chamber 66 to be set between zero and fifteen centimeters $H_2O$ gage (zero to approximate 0.2 pounds per square inch gage). A bleeder conduit or line 76 enables a back flow of gas from chamber 66 to enter chamber 58, with an adjustable needle valve 78 forming a restriction in the line to limit the flow rate (gas flows in the opposite direction, from chamber 58 to chamber 66, are transmitted through check valve 68). Needle valve 78 may be adjusted from a full-open position, at which the gas flow through bleeder line 76 is substantially unrestricted, to a completely closed position.

Dynamic control of the breath assist mechanism 38 starts at a pressure transducer 80 that is divided into two compartments by a diaphragm 82, one compartment 59 being pressure-equalized with chamber 58 by means of a connecting tube 84, and the other compartment 61 equalizing in pressure with constant pressure chamber 66 by means of a tap 86 from a second connecting tube 88. The other end of tube 88 enters compartment 20 of demand regulator 18 to equalize the pressure therein with the constant pressure in chamber 66.

It can thus be seen that the two compartments of pressure transducer 80 are able to compare the variable gas pressure in chamber 58 (which is equal to the pressure within the conduit system 46 when the conduit outlet port 56 is uncovered) with the constant pressure in chamber 66, the latter pressure being positively maintained as a constant reference point. When the pressure in chamber 66 exceeds that in chamber 58 by a predetermined threshold amount, transducer diaphragm 82 flexes sufficiently to make an electrical contact (not shown) and thereby transmit a signal to a breath assist control circuit 90 over line 92. In the control circuit 90 the signal is processed in a manner critical to the invention so as to actuate the breath assist mechanism 38 in a predetermined intermittent manner. At the same time, transducer 80 also transmits a signal to piston control 64 over line 91, causing piston 62 to move against the diaphragm 60 and block outlet port 56.

The trigger level of transducer 80 is adjustable within a suitable range such as, for example, 0.05 centimeter $H_2O$ to 1.0 centimeter $H_2O$, to permit the selection of a variety of patient inspiratory efforts necessary to trigger the breath assist. In any case the trigger level of transducer 80 is less than that of demand regulator 18. The settings of needle valve 78 and transducer 80 are normaly determined by the expected voluntary inhalation flow rate produced by the patient 16; gas flows through bleeder line 76 should be substantially unrestricted by needle valve 78 for flow rates that are substantially less than the expected inhalation rate. At such low flow rates the flow through bleeder line 76 is sufficient to substantially equalize the pressures in chambers 58 and 66, thereby inhibiting transducer 80 from producing a control signal. Larger back flows of gas are established from chamber 58 to the patient through conduit branch 54 when the patient attempts to draw a breath. When this occurs the flow of gas through bleeder line 76 is restricted by needle valve 78 to a rate less than that which is necessary to equalize the pressures in chambers 58 and 66, thereby producing a pressure differential between the two chambers that causes transducer 80 to trigger and produce a control signal in response to a patient's effort to breath.

Figure 2:
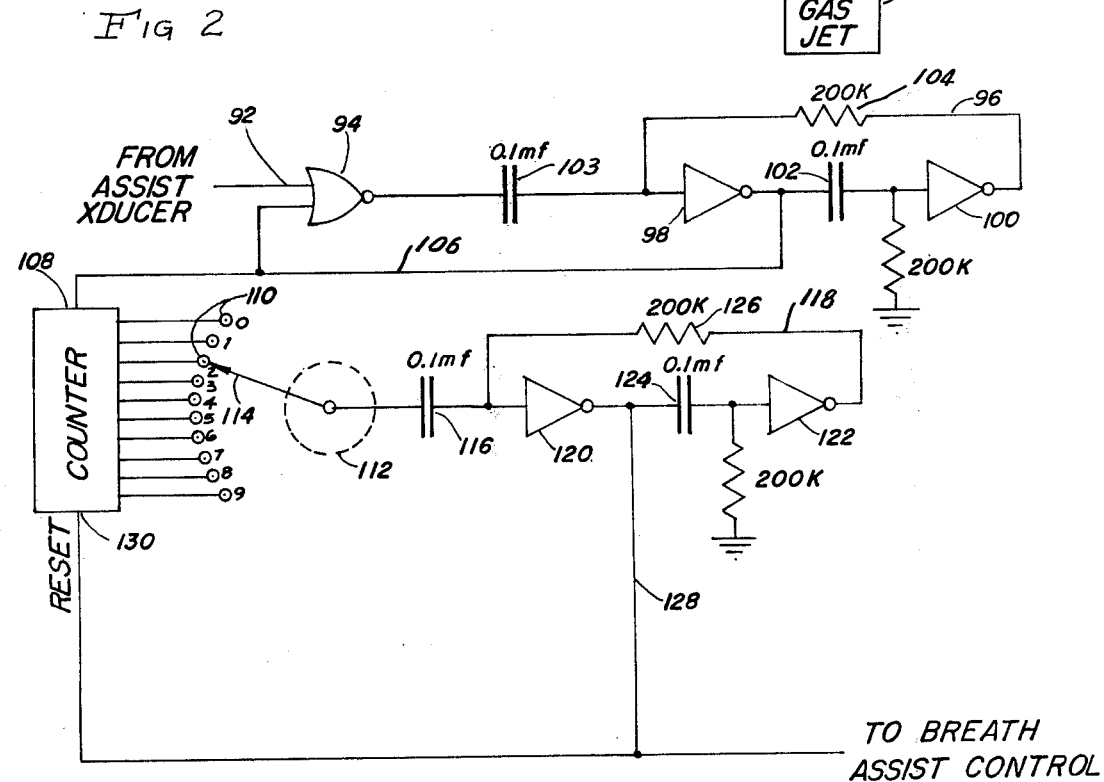
FIG. 2 is a circuit diagram of a control circuit which governs alternation between assisted and spontaneous breathing modes.

Referring to FIG. 2 for details of the control circuit 90, line 92 from the assist transducer 80 is connected to one input of a NOR gate 94. A capacitor 103 is connected between NOR gate 94 and one-shot circuit 96, which includes a pair of cross-coupled inverters 98 and 100, a capacitor 102 connected in the first cross-coupling branch between the output of inverter 98 and the input to inverter 100, and a resistor 104 in the other cross-coupling branch, is connected to the output of NOR gate 94 by means of coupling capacitor 103. The output of the one-shot 96 is delivered over line 106 to the counting input of a binary counter 108, and in addition is fed back to the other input of NOR gate 94 to ensure that capacitor 102 has sufficient time to charge when a control signal is received from transducer 80.

The counter 108 is illustrated as having ten output stages 110, numbered 0 through 9 in the drawing, although it should be understood that the capacity of the counter is a matter of choice and will be determined primarily by the maximum desired ratio of spontaneous breaths to assisted breaths. A rotatable knob 112 (indicated in dashed-lines) carries a contact arm 114 that can be set on any of the output terminals 110 of counter 108. Contact arm 114 is electrically connected through capacitor 116 to a second one-shot 118, similar in design to one-shot 96, with inverters 120 and 122, a capacitor 124 in one cross-coupling branch, and a resistor 126 in the other cross-coupling branch. One-shot 118 produces an output signal over an output line 128 to actuate breath assist control switch 44 in response to an appropriate output signal being produced by one-shot 118. Line 128 is also connected to the reset input 130 of counter 108 such that the counter is reset to its initial state each time it has counted up to the output stage selected by switch arm 114.

In the embodiment shown, the signal at line 92 is normally at a relatively low voltage or OFF state. Assist transducer 80 provides an ON signal when a patient's attempt to breathe is sensed.

In operation, the described apparatus can be used to alternate the respirator system between spontaneous and assisted breathing modes in an efficient and controlled manner, such that the patient can gradually be weaned away from the respirator as he regains his breathing power. Selector switch 112 is initially set at the particular counter output terminal 110 corresponding to the desired ratio of spontaneous to assisted breaths. For example, if two spontaneous breaths are desired for each assisted breath, contact arm 114 is set at the "two" counter terminal, as illustrated in FIG. 2. Different spontaneous to assisted breathing ratios may be had by merely adjusting the selector switch 112 so that the contact arm 114 connects with a different counter terminal.

Assuming the patient has just finished the end of an expiration and is about to begin a new breath, piston 62 is in a withdrawn position uncovering conduit outlet port 56, and the pressures in chambers 58 and 66 are substantially equal. When the patient begins to suck in at the beginning of the next breath, a partial vacuum is created in chamber 58 that, because of the restriction imposed by needle valve 78, can only partially be made up by a flow of air through bleeder line 76 from chamber 66. The pressure imbalance thus created between chambers 58 and 66 causes the diaphragm 82 of assist transducer 80 to flex and establish an output signal. Piston control 64 is thereby actuated to drive piston 62 forward into diaphragm 60, blocking outlet port 56. At the same time a signal is applied over line 92 to the control circuit 90, turning the input to NOR gate 94 ON and its output OFF. This results in a change of state of the succeeding inverters 98 and 100 and a charging of capacitor 102, such that an output is produced over line 106 to counter 108. Assuming the counter is initially reset, the applied signal causes a positive output to be produced at the "zero" output terminal 110. If selector switch 112 has been set to one of the other counter output terminals as shown in FIG. 2, processing of the signal through control circuit 90 is terminated at this point and breath assist control switch 44 is left in an inactive state. If, however, switch 112 has the setting as illustrated in FIG. 2, that is, at counter terminal 2, the third such signal applied over line 92 will be processed as heretofore described so as to cause a signal to be applied by means of contact arm 114 through switch 112, and through coupling capacitor 116 to effect a change of state in inverters 120 and 122, thus charging capacitor 124 such that an output signal will be produced over line 128 so as to activate breath assist control switch 44 and to reset counter 108. As the patient continues to suck in air, a negative pressure is produced in compartment 22 of demand regulator 18 which becomes great enough to draw in diaphragm 24, moving stopper 32 away from opening 28 so that breathing air can flow from mixing valve 14, through demand regulator 18 and conduit system 46, to the patient, who now completes the inspiration portion of a spontaneous breath. By the time the patient is ready to exhale, the pressure within chamber 58 will have increased by air flow through bleeder line 76 to a level at which transducer 80 permits piston 62 to retract. Outlet port 56 is thereby uncovered, allowing expired air to flow out of the system through orifices 74.

Each succeeding attempt by the patient to breathe triggers assist transducer 80 to advance the counting output of counter 108 by one output state. Demand regulator 18 supplies breathing air for each spontaneous breath until the counter output reaches the preselected setting of switch 112. When this happens a triggering signal is transmitted over contact arm 114 and through capacitor 116 to one-shot 118. The resulting one-shot output over line 128 resets counter 108 and completes an actuating circuit for breath assist control switch 44. Actuation of switch 44 drives piston 40 into cylinder 42, forcing the breathing air therein through the conduit network 46 to the patient. In addition to providing the patient with an assisted breath, the movement of piston 40 increases the pressure within conduit system 46 to a level at which the initiation of a spontaneous air flow from demand regulator 18 is prevented. Piston 40 is thereafter withdrawn, creating a negative pressure sufficient to draw a new supply of breathing air into cylinder 42 from demand regulator 18, while check valve 48 isolates the patient from the negative pressure.

It can thus be seen that the patient is allowed to breathe spontaneously for a number of breaths equal to the particular output 110 to which selector switch 112 is set, followed by an assisted breath, the breathing air being efficiently supplied only when required by the patient. Thereafter the pattern of the ratio of spontaneous to assisted breaths is repeated for as long as the selector switch 112 is left in place. If it is initially desired to give the patient only assisted breaths, contact arm 114 is set on the "zero" counter output terminal 110. Every succeeding attempt to breathe is sensed by assist transducer 80, which causes counter 108 to produce an output at the "zero" terminal and thereby actuate breath assist control switch 44. When the patient has recovered sufficiently to breathe at least partially on his own, spontaneous breaths may be introduced by setting selector switch 112 to a higher order counter output. By gradually increasing the setting of selector switch 112, the patient is allowed to breathe more and more on his own and can be safely weaned away from the respirator system while still retaining the benefit of occasional assisted breaths. While theoretically counter 108 could have any number of output stages, it is unlikely that more than about 20 would be required. Within this range the breathing assistance rendered the patient can be safely and conveniently controlled by the respirator operator, who is able to make minute-by-minute adjustments based on the patient's observed condition.

While a particular embodiment of the invention has been shown and described, numerous additional modifications and variations are possible in light of the above teachings. For example, an override mechanism could be added to actuate the breath assist should the patient fail to breathe within a predetermined time interval, or a plurality of assisted breaths could be alternated with a single spontaneous breath. It is therefore intended that the scope of the invention be limited only in and by the terms of the appended claims.

What is claimed is:

1. A respirator system comprising:
   means for transmitting gas suitable for breathing to a patient;
   means for supplying said gas to said means for transmitting;
   means for sensing and producing an electronic signal indicative of the patient's efforts to breathe;
   means for counting and producing an electronic signal indicative of a predetermined number of said efforts to breath made by the patient;
   electronic circuit means for determining and preselecting a desired ratio of spontaneous breaths and producing an electronic signal indicative thereof to assisted breaths to be furnished to the patient;
   first means for providing said gas to said means for supplying at a pressure suitable for a spontaneous breath in response to said patient's efforts to breathe;
   second means for providing said gas to said means for supplying at a pressure suitable for an assisted breath in response to said signal produced by said means for determining and preselecting a desired ratio of spontaneous breaths to assisted breaths to be furnished to the patient; and
   means for preventing the superposition of an assisted breath upon a spontaneous breath.

2. The respirator system of claim 1, wherein said means for sensing the patient's efforts to breath comprise:
   means to maintain a constant reference pressure;
   a constant reference pressure chamber maintained at said constant reference pressure;

a first variable reference pressure chamber in first directional fluid communication with said constant reference pressure chamber;

an outlet port situate within said first variable reference pressure chamber in fluid communication with the patient by means of a conduit;

first flexible, resilient diaphragm means operable to open and close said outlet port;

means for providing restrictive second directional fluid communication between said constant reference pressure chamber and said first variable reference pressure chamber;

assist transducer means in fluid communication with said constant reference pressure chamber and with said first variable reference pressure chamber for furnishing electronic signal responsive to differential pressures therebetween;

second flexible, resilient diaphragm means situate in said assist transducer means for responding to pressures in said constant reference pressure chamber and pressures in said first variable reference pressure chamber;

breath assist control circuit means responsive to said electronic signal from said assist transducer means and developing an electronic signal therefrom;

breath assist control switch means responsive to said electronic signal from said control circuit means and developing a further electronic output signal therefrom;

first piston means responsive to said further electronic output signal and operative to charge a quantity of breatheable gas into said means for supplying in response to said further electronic output signal;

piston control means responsive to said electronic signal from said breath assist control circuit means and developing another further electronic output signal therefrom;

second piston means responsive to said another further electronic output signal and operative to open and close said outlet port situate within said first variable reference pressure chamber; and demand regulator means responsive to a patient's efforts to breathe, and in fluid communication with said assist transducer means and said constant reference pressure chamber.

3. The system of claim 2, wherein said second flexible resilient diaphragm means separates a pressure applied from said constant reference pressure chamber from a pressure applied from said first variable reference pressure chamber.

4. The system of claim 3, wherein a pressure in said first variable pressure chamber varies over a range from a reference pressure as maintained in said constant reference pressure chambers, to less than the reference pressure, in accordance with the patient's efforts to breathe.

5. The system of claim 4, wherein a predetermined threshold variation of pressure in said first variable reference pressure chamber causes flexure of said second flexible resilient diaphragm means so as to make an electrical contact.

6. The system of claim 5, wherein said predetermined threshold variation of pressure in said first variable reference pressure chamber is less than the variation of pressure in said pressure sensing chamber sufficient to cause flexure of said third flexible resilient diaphragm means.

7. The system of claim 2, wherein said demand regulator means comprises:

a reference pressure chamber in fluid communication with said constant reference pressure chamber;

third flexible, resilient diaphragm means forming one wall of said reference pressure chamber;

a pressure sensing chamber having said third flexible, resilient diaphragm means as a common wall between said pressure sensing chamber and said reference pressure chamber;

an inlet chamber in fluid communication with said means for supplying and having a central opening into said pressure sensing chamber in a common dividing wall therebetween;

a rod connected between said third flexible, resilient diaphragm means and a stopper operable to open and close said central opening in response to mechanical movement of said third flexible, resilient diaphragm means; and check valve means to communicate a patient's inspiratory efforts to said pressure sensing chamber while isolating expiratory pressures therefrom.

8. The system of claim 7 wherein a pressure in said pressure sensing chamber varies from a reference pressure as maintained in said constant reference pressure chamber to less than the reference pressure in accordance with the patient's efforts to breathe.

9. The system of claim 8, wherein a variation of pressure in said pressure sensing chamber sufficient to cause flexure of said third flexible resilient diaphragm means admits said gas suitable for breathing to said inlet chamber and to said means for transmitting.

10. The system of claim 9, wherein said breath assist control circuit means comprises:

electronic logic means responsive to said means for sensing;

first one-shot circuit means responsive to said electronic logic means;

means responsive to said first one-shot circuit means for counting output signals furnished by said one-shot circuit means;

second one-shot circuit means responsive to and coupled to said means for counting and furnishing its signal output to said breath assist control switch.

11. The system of claim 10, wherein said means for counting includes a plurality of integrally ordered output terminals, each of which becomes energized in response to the same integrally ordered number of output signals furnished by said one-shot circuit means.

12. The system of claim 11, wherein said second one-shot circuit means is coupled to said means for counting by means of a selector switch adjustable by means of an adjustable contact arm to select each of said plurality of integrally ordered output terminals so as to select a desired ratio of spontaneous breaths to assisted breaths.

13. The system of claim 12, wherein the adjustment of said selector switch by means of said adjustable contact arm to one of said plurality of integrally ordered output terminals thereby selects the ratio of spontaneous breaths to assisted breaths defined by the ordinal number of said one of said plurality of integrally ordered output terminals as numerator to one as denominator.

14. The system of claim 1, wherein said means for counting and producing an electronic signal indicative of a predetermined number of said efforts to breathe made by the patient comprise:

electronic logic means responsive to said means for sensing and producing an electronic signal indicative of the patient's efforts to breathe;

first one-shot circuit means responsive to said electronic logic means;

electronic counter means responsive to said first one-shot circuit means responsive to said electronic logic means;

adjustable switch means receiving output signal from said electronic counter means; and second one-shot circuit means receiving the output signal from said adjustable switch means.

15. The system of claim 14, wherein said electronic counter means includes a plurality of integrally ordered output terminals, each of which may be energized in response to the same integrally ordered number of output signals from said first one-shot circuit means.

16. The system of claim 15, wherein said plurality of integrally ordered output terminals is coupled to said means for determining and preselecting a desired ratio of spontaneous breaths to assisted breaths.

17. The system of claim 16, wherein said means for determining and preselecting a desired ratio of spontaneous breaths to assisted breaths comprises:

a selector switch having an adjustable contact arm in adjustable contact with said counter;

second one-shot circuit means responsive to output signal from said electronic counter means having said adjustable contact arm of said selector switch coupled to its input terminal.

18. The system of claim 17, wherein said adjustable contact arm is adjustable over said plurality of integrally ordered output terminals of said electronic counter means.

19. The system of claim 18, wherein said second one-shot circuit means is effective to reset said electronic counter means in response to signal generated therein as a result of preselection of a desired ratio of spontaneous breaths to assisted breaths.

20. The system of claim 1, wherein said means for determining and preselecting a desired ratio of spontaneous breaths and producing an electronic signal indicative thereof to assisted breaths to be furnished to the patient comprises:

electronic logic means responsive to said means for sensing and producing an electronic signal indicative of the patient's efforts to breathe;

first one-shot circuit means responsive to signal output from said electronic logic means;

means responsive to said first one-shot circuit means for counting output signals furnished by said first one-shot circuit means; and second one-shot circuit means responsive to and coupled to said means for counting.

21. The system of claim 20, wherein said means for counting includes a plurality of integrally ordered output terminals, each of which becomes energized in response to the same integrally ordered number of output signals furnished by said first one-shot circuit means.

22. The system of claim 21, wherein said second one-shot circuit means is coupled to said means for counting by means of a selector switch adjustable by means of an adjustable contact arm to select each of said plurality of integrally ordered output terminals so as to select a desired ratio of spontaneous breaths to assisted breaths.

23. The system of claim 22, wherein the adjustment of said selector switch by means of said adjustable contact arm to one of said plurality of integrally ordered output terminals thereby selects the ratio of spontaneous breaths to assisted breaths defined by the ordinal number of said one of said plurality of integrally ordered output terminals as numerator to one as denominator.

24. The respirator system of claim 7, wherein said first means for providing said gas comprises;

piston control means responsive to said means for sensing, for controlling the position of a piston;

first flexible resilient diaphragm means responsive to the position of said piston;

variable pressure chamber means in one-way fluid communication to a constant pressure chamber and in fluid communication with an expiratory branch having an outlet port within said variable pressure chamber means which port may be opened or closed in response to the position of said piston as controlled by said piston control means;

bleeder conduit means between said variable pressure chamber means and said constant pressure chamber permitting limited flow rate from said constant pressure chamber to said variable pressure chamber means; and demand regulator means in fluid communication with said constant pressure chamber.

25. The system of claim 24, wherein said demand regulator means comprises:

a flexible resilient diaphragm that separates a constant reference pressure chamber from a sensing chamber;

an inlet chamber in fluid communication with said means for supply gas, said inlet chamber being separated from said sensing chamber by a wall having a central opening;

a stopper situate in said inlet chamber, and attached to one end of a rod whose other end extends through said central opening to said flexible resilient diaphragm such that said stopper is driven by the flexure of said diaphragm to open or close said central opening and thus admit gas from said means for supplying to flow into said inlet chamber;

means for transmitting said gas from said inlet chamber to a patient.

26. The system of claim 25, wherein said means for transmitting includes check valve means and means for filtering and humidifying said gas.

27. The system of claim 1, wherein said second means for providing gas comprises:

breath assist control switch means responsive to signal output from control circuit means;

piston and cylinder means responsive to command signal from said breath assist control switch means for containing a volume of said gas when said piston is retracted from said cylinder and operable upon said command to force said volume of gas into said means for transmitting.

* * * * *

UNITED STATES PATENT OFFICE
CERTIFICATE OF CORRECTION

Patent No. 4,141,356                     Dated   February 27, 1979

Inventor(s)  Paul R. Smargiassi

It is certified that error appears in the above-identified patent and that said Letters Patent are hereby corrected as shown below:

Column 4, Line 47:  "humidyfying" should read -- humidifying --

Column 5, Line 59:  "normaly" should read -- normally --

Column 6, Line 30:  "A rotatable knob" should read -- An adjustable switch --

Signed and Sealed this

Sixth    Day of   November 1979

[SEAL]

Attest:

RUTH C. MASON
Attesting Officer

LUTRELLE F. PARKER
Acting Commissioner of Patents and Trademarks